United States Patent [19]
Handrick

[11] 3,948,956
[45] Apr. 6, 1976

[54] PROCESS FOR THE PURIFICATION OF CRUDE TRIMELLITIC ANHYDRIDE
[75] Inventor: Kurt Handrick, Essen, Germany
[73] Assignee: Bergwerksverband GmbH, Essen, Germany
[22] Filed: Oct. 29, 1974
[21] Appl. No.: 518,868

Related U.S. Application Data
[63] Continuation of Ser. No. 280,104, Aug. 14, 1974, abandoned, which is a continuation-in-part of Ser. No. 46,932, June 1, 1970, abandoned.

[30] Foreign Application Priority Data
May 31, 1969 Germany............................ 1943562

[52] U.S. Cl. ............................................. 260/346.3
[51] Int. Cl.² ....................................... C07D 307/89
[58] Field of Search ...................... 260/346.3, 346.4

[56] References Cited
UNITED STATES PATENTS
2,888,465  5/1959  Hodes ............................. 260/346.3

Primary Examiner—John D. Randolph
Assistant Examiner—Bernard I. Dentz
Attorney, Agent, or Firm—Michael J. Striker

[57] ABSTRACT

Commercial grade crude trimellitic acid anhydride containing free trimellitic acid and other impurities is purified by forming a suspension of the trimellitic acid anhydride in a mixture of acetic acid anhydride, acetic acid and benzene at a temperature of about the boiling point of the mass, the acetic acid anhydride being used in an excess up to about 200% by weight over the stoichiometric amount and the benzene being used in an amount up to 6 times the weight of the anhydride and recovering the purified trimellitic acid anhydride from the mass.

9 Claims, No Drawings

PROCESS FOR THE PURIFICATION OF CRUDE TRIMELLITIC ANHYDRIDE

CROSS-REFERENCE TO RELATED APPLICATIONS

This application is a continuation of my prior application Ser. No. 280,104, filed Aug. 14, 1972, which in turn is a continuation-in-part of my application Ser. No. 46,932, filed June 1, 1970, both now abandoned.

BACKGROUND OF THE INVENTION

The invention relates to a process for purification of trimellitic acid anhydride. From U.S. Pat. No. 2,888,465 it is known that trimellitic acid and acetic acid anhydride can be reacted in the presence of normally liquid alkylbenzenes, such as, toluene or xylene, at a temperature between 80° and 135°C, preferably 95° to 150°C, until a homogeneous liquid phase is formed. From this liquid phase the trimellitic acid anhydride can be obtained. However, it appears desirable to improve the yield of this reaction and the quality of the acid anhydride which is obtained in several crystal fractions after cooling.

The patent also mentions the use of benzene as solvent provided the reaction is carried out at an elevated temperature and elevated pressure. However, in this case, the formation of a homogeneous liquid phase is likewise necessary. Therefore and in view of the very low solubility of trimellitic acid anhydride in benzene even at elevated temperature large amounts of benzene and a temperature above 135°C are necessary. Both of these circumstances are undesirable since they result in an impairment of the quality of the product and of the yield.

SUMMARY OF THE INVENTION

The invention is based on the finding that trimellitic acid anhydride of high purity can be obtained at high yields if the trimellitic acid anhydride is suspended in a mixture of acetic acid anhydride, acetic acid and benzene and the suspension reaction is carried out around the boiling point of the mixture. In this case no homogeneous liquid phase is formed but the purified anhydride is obtained by separating it from the suspension.

The acetic acid anhydride in this case should be used in an excess up to about 200% by weight of the stoichiometric amount and the benzene should be employed in an amount between 2 to 3 times and up to 6 times the weight of the trimellitic acid anhydride.

DETAILS OF THE INVENTION AND PREFERRED EMBODIMENTS

It is surprising that trimellitic acid anhydride can be purified successfully and with a good yield in spite of the fact that no homogeneous solution is obtained.

A comparatively low reaction temperature is used for the reaction, the temperature being in the range of 80° to 90°C. Since the reaction is strongly exothermic when practicing the invention on a large scale, it is advisable to add the acetic acid anhydride only gradually to the mixture of trimellitic acid anhydride, acetic acid and benzene which has previously been brought to up to the reaction temperature. It is also possible to introoduce the trimellitic acid anhydride gradually into the solvent mixture which has been heated to the boiling point range.

To calm down the reaction it is also preferable to employ a large excess of benzene. The reaction is preferably carried out in two to three times and at most six times the amount of benzene relative to the weight and amount of trimellitic acid.

Usually a comparatively small stoichiometric excess of the acetic acid anhydride is sufficient. However, if the invention is applied to a highly impure trimellitic acid anhydride it is preferred to employ a relatively larger amount of acetic acid anhydride. The amount of acetic acid anhydride in general may be up to 200% by weight of the stoichiometric amount but preferably is in the range of 10 to 30% by weight of that amount.

The time for the reaction is between about 20 and 40 minutes.

At the completion of the reaction the mixture is cooled down to room temperature. The trimellitic acid anhydride is then obtained more or less quantitatively in the form of crude crystals by filtering the anhydride from the solvent mass, washing it with benzene and drying it.

The high purity of the trimellitic acid anhydride obtained by the process of the invention appears in particular in case of esterification with methanol. Heretofore only a liquid trimellitic acid trimethyl ester was known as the product of this esterification. By the process of the invention, the ester can be obtained in crystalline form, having a melting point of 36°C.

If the reaction with benzene is carried out at higher temperatures, for instance 130°C, and upon application of pressure, the yield, color and acid number of the trimellitic acid anhydride are impaired.

The purification in the process of the invention is due to the high selectivity of benzene which keeps contaminations and discoloration components in solution while the trimellitic acid anhydride remains practically insoluble.

A further advantage of the process of the invention is that an overheating of the reaction mixture is avoided since the reaction temperature is determined by the boiling point range of the mixture. The invention also has the advantage of an easy distillative separation of the filtrate into benzene, acetic acid and residual acetic acid anhydride because of the high boiling point differential. Benzene and acetic acid anhydride can then be recycled into the process.

The high degree of purity of the trimellitic acid anhydride of the process of the invention is important for use of the product in the synthetic resin and plasticizer industry.

The following examples will further illustrate the invention.

EXAMPLE 1

The trimellitic acid anhydride used as the starting point in this case was a commercially available grade of anhydride which had an acid number of 868 and an APHA color number (solution in dimethylformamide) of 90. In addition to free trimellitic acid which is always present in the commercial grade trimellitic acid anhydride, there were present about 2.5% of other contaminations including terephthalic acid, isophthalic acid, pyromellitic acid anhydride and trimesic acid. One kg of the trimellitic acid anhydride was mixed with 2.5 1 benzene, 150 ml acetic acid anhydride and 500 ml glacial acetic acid and subjected to a further anhydrizing operation for a reflux time of 20 minutes at a temperature of 83° to 84°C.

There were obtained 966 gr. of trimellitic acid anhydride with an acid number of 875 and the color number of 20. The latter had been determined by dissolving 10 gr of the trimellitic acid anhydride in 100 ml dimethyl formamide at 20°C.

The product obtained in the above example contained only traces of terephthalic acid and had a degree of purity of at least 99.5%.

EXAMPLE 2

The starting product in this case was a crude trimellitic acid anhydride with an acid number of 870 and a nitrogen content of 0.11%. It contained, in addition to free trimellitic acid, about 2% of nitrophthalic acids and nitrotrimellitic acid anhydride. Twenty kg of this product were heated together with 50 l benzene, 8 l glacial acetic acid and 2 l acetic acid anhydride to a reflux temperature of 83°–84°C in an enameled reaction vessel for 30 minutes while stirring. The crystal slurry was then cooled at 20°C. The crystals were removed by centrifugal force, were washed with a little benzene and dried at 120°C. in a low vacuum.

The yield of purified trimellitic acid anhydride was 19.3 kg which corresponded to 96.5% yield by weight of the theoretical yield. The product had a theoretical acid number of 876 and a nitrogen content below 0.005%.

The filtrate had a yellow coloration and after distillation and adding small amounts of fresh acetic acid anhydride was used for the next run.

10 Gram of the purified trimellitic acid anhydride were dissolved in 100 ml dimethyl formamide at 20°C to obtain the color number. It was found that the color number (APHA number) was 10. This contrasted with a color number of 240 for the crude trimellitic acid anhydride used as starting product.

I claim:

1. A process for purification of crude trimellitic anhydride that is contaminated with small proportions of trimellitic acid and one or more additional benzenecarboxylic acids or anhydrides to convert the trimellitic acid contained therein to trimellitic anhydride and simultaneously remove a substantial proportion of the other contaminants which process comprises forming a suspension of the crude solid trimellitic anhydride particles in a liquid medium consisting of benzene, acetic anhydride, and glacial acetic acid in which trimellitic anhydride is only sparingly soluble at the boiling point of the medium in such proportions that the amount of benzene in the medium is at least 2 and at most 6 times the weight of the trimellitic anhydride contained therein and the amount of acetic anhydride is sufficient to convert substantially all of the trimellitic acid in the crude trimellitic anhydride to trimellitic anhydride and heating the said suspension at about the boiling point of the suspending medium for a period at least sufficient to convert substantially all of the trimellitic acid to trimellitic anhydride, and subsequently separating the thus-purified suspended trimellitic anhydride particles from the suspension.

2. A process as defined in claim 1 in which the amount of benzene that is included in the suspending medium is at least 2 and at most 3 times the weight of the trimellitic anhydride that is suspended therein.

3. A process as defined in claim 1 in which the suspension is heated at a temperature between 80° and 90°C for a period between 20 and 40 minutes.

4. A process as defined in claim 1 in which the suspension is formed by gradually adding the acetic acid and acetic anhydride to a preliminarily heated suspension of the crude trimellitic anhydride in the benzene.

5. A process as defined in claim 1 in which the suspension is formed by gradually adding the crude trimellitic anhydride to the preliminarily heated medium consisting of acetic acid, acetic anhydride, and benzene.

6. A process as defined in claim 1 in which the crude trimellitic anhydride that is treated contains besides trimellitic acid a total of about 2.5% by weight of one or more benzenecarboxylic acids of the group consisting of terephthalic acid, isophthalic acid, pyromellitic anhydride and trimesic acid.

7. A process as defined in claim 1 in which the crude trimellitic anhydride that is treated contains besides trimellitic acid a total of about 2.0% by weight of one or more benzenecarboxylic acids of the group consisting of nitrophthalic acids and nitrotrimellitic anhydride.

8. A process as defined in claim 1 in which the suspending medium consists of 2.5 liters of benzene, 0.5 liter of glacial acetic acid, and 0.15 liter of acetic anhydride per kilogram of trimellitic anhydride.

9. A process as defined in claim 1 in which the suspending medium consists of 2.5 liters of benzene, 0.4 liter of glacial acetic acid, and 0.1 liter of acetic anhydride per kilogram of trimellitic anhydride.

* * * * *